United States Patent [19]

Kameswaran

[11] Patent Number: 5,347,016
[45] Date of Patent: Sep. 13, 1994

[54] N-OXYGENATED ARYLPYRROLE INTERMEDIATES FOR INSECTICIDAL, ACARICIDAL AND NEMATICIDAL AGENTS

[75] Inventor: Venkataraman Kameswaran, Princeton Junction, N.J.

[73] Assignee: American Cyanamid Company, Wayne, N.J.

[21] Appl. No.: 61,904

[22] Filed: May 14, 1993

Related U.S. Application Data

[62] Division of Ser. No. 818,319, Jan. 8, 1992, Pat. No. 5,232,979, which is a division of Ser. No. 447,726, Dec. 8, 1989, Pat. No. 5,102,904.

[51] Int. Cl.$^5$ .................. C07D 207/46; C07D 407/10
[52] U.S. Cl. ..................................... 548/531; 548/526
[58] Field of Search ........................ 548/526, 531

[56] References Cited

U.S. PATENT DOCUMENTS 2,987,437  6/1961  Hessel ................................. 167/33
3,050,442  8/1962  Bijloo et al. ........................ 167/33

OTHER PUBLICATIONS

Annali di Chimica (Rome) 50, pp. 1627–1634 (1960).
Bulletin de la Societe Chimique de France, p. 4679 (1968).
Bulletin de la Societe Chimique de France, pp. 4330–4341 (1970).
Journal of Organic Chemistry, 38, pp. 173–174 (1973).

*Primary Examiner*—David B. Springer
*Attorney, Agent, or Firm*—John W. Hogan, Jr.

[57] ABSTRACT

Novel N-oxygenated arylpyrrole compounds which are effective for the control of insects, acarids and nematodes are described. A method for the insecticidal, acaricidal and nematicidal use of said compounds and a method for the preparation of said compounds are presented.

1 Claim, No Drawings

N-OXYGENATED ARYLPYRROLE INTERMEDIATES FOR INSECTICIDAL, ACARICIDAL AND NEMATICIDAL AGENTS

BACKGROUND OF THE INVENTION

This is a division of co-pending application Ser. No. 07/818,319, filed on Jan. 8, 1992, U.S. Pat. No. 5,232,979, which is a division of application Ser. No. 07/447,726, filed Dec. 8, 1989, now U.S. Pat. No. 5,102,904, issued Apr. 7, 1992.

SUMMARY OF THE INVENTION

The present invention describes N-oxygenated arylpyrrole compounds that are highly effective insecticidal, acaricidal and nematicidal agents useful for the control of insect, acarid and nematode pests and for protecting agronomic crops, both growing and harvested, against the ravages of said pests.

The N-oxygenated arylpyrrole compounds of the present invention have the structural formula I:

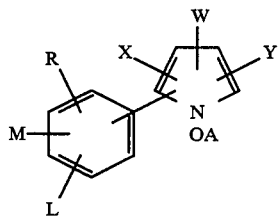

(I)

wherein
X is H, F, Cl, Br, I, $CF_3$ or CN;
Y is H, F, Cl, Br or I;
W is CN or $NO_2$;
A is H, $C_1$-$C_4$ alkyl or $C_2$-$C_4$ monohaloalkyl, each optionally substituted with from one to three additonal halogen atoms, one cyano, one hydroxy, one or two $C_1$-$C_4$ alkoxy groups each optionally substituted with one to three halogen atoms, one $C_1$-$C_4$ alkylthio, one $C_1$-$C_4$ carbalkoxy, one $C_1$-$C_6$ alkylcarbonyloxy, one $C_2$-$C_6$ alkenylcarbonyloxy, one benzenecarbonyloxy, or chloro, dichloro, or methyl substituted benzenecarbonyloxy, one phenyl optionally substituted with $C_1$-$C_3$ alkoxy or with one to three halogen atoms, one phenoxy optionally substituted with one to three halogen atoms, or one benzyloxy optionally substituted with one halogen substituent;
$C_3$-$C_5$ alkenyl optionally substituted with one to three halogen atoms;
$C_3$-$C_5$ alkynyl optionally substituted with one halogen atom; or

D is $C_1$-$C_6$ alkyl, $C_2$-$C_4$ alkenyl, $C_1$-$C_4$ alkoxy, phenyl or phenoxy, all optionally substituted with 1 to 3 halogens, di-($C_1$-$C_4$ alkyl)amino or $N(CH_2)_m$;
m is an integer of 3, 4, 5, 6 or 7;
L is H, F, Cl or Br; and
M and R are each independently H, $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, cyano, F, Cl, Br, I, nitro, $CF_3$, $R_1CF_2Z$, $R_2CO$ or $NR_3R_4$; and when M and R are on adjacent positions and taken with the carbon atoms to which they are attached they may form a ring in which MR represents the structure:

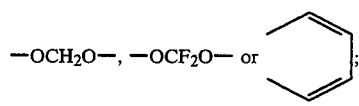

Z is $S(O)_n$ or O;
$R_1$ is H, F, $CHF_2$, CHFCl or $CF_3$;
$R_2$ is $C_1$-$C_3$ alkyl, $C_1$-$C_3$ alkoxy or $NR_3R_4$;
$R_3$ is H or $C_1$-$C_3$ alkyl;
$R_4$ is H, $C_1$-$C_3$ alkyl or $R_5CO$;
$R_5$ is H or $C_1$-$C_3$ alkyl; and
n is an integer of 0, 1 or 2.

DETAILED DESCRIPTION OF THE INVENTION

The compounds of the present invention are excellent insecticidal, acarididal and nematicidal agents. The invention provides a method for controlling undesirable pests by contacting the pests, their breeding grounds, food supply or habitat with a pesticidally effective amount of an N-oxygenated arylpyrrole compound. Preferred groups of N-oxygenated arylpyrroles of the present invention are illustrated by formula II, formula III and formula IV.

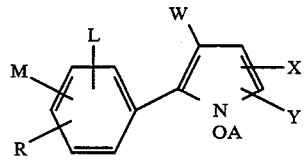

(II)

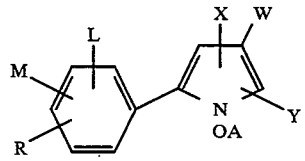

(III)

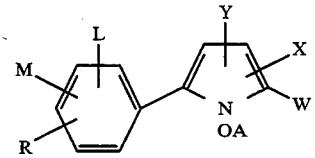

(IV)

wherein A, L, M, R, W, X and Y are as described above.

Preferred N-oxygenated arylpyrroles of the invention are those in which
A is hydrogen or $C_1$-$C_4$ alkyl optionally substituted with one $C_1$-$C_4$ alkoxy group;
W is CN or $NO_2$;
X is Cl, Br or $CF_3$;
Y is Cl or Br;
R is F, Cl, Br, $CF_3$ or $OCF_3$;
M is H, F, Cl or Br; and
L is H or F.

The N-oxygenated arylpyrrole compounds of formula I, wherein A is hydrogen, W is CN and X, Y, L, M and R are as described above, may be prepared by reacting methyl benzoate or a substituted methyl benzoate represented by the structural formula V:

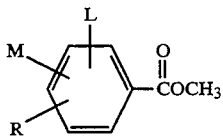

wherein
L is H, F, Cl or Br; and
M and R are each independently H, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, cyano, F, Cl, Br, I, nitro, $CF_3$, $R_1CF_2Z$, $R_2CO$ or $NR_3R_4$; and when M and R are on adjacent positions and taken with the carbon atoms to which they are attached they may form a ring in which MR represents the structure:

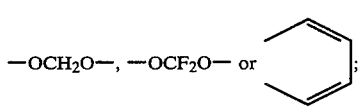

Z is $S(O)_n$ or O;
$R_1$ is H, F, $CHF_2$, CHFCl or $CF_3$;
$R_2$ is $C_1$–$C_3$ alkyl, $C_1$–$C_3$ alkoxy or $NR_3R_4$;
$R_3$ is H or $C_1$–$C_3$ alkyl;
$R_4$ is H, $C_1$–$C_3$ alkyl or $R_5CO$;
$R_5$ is H or $C_1$–$C_3$ alkyl; and
n is an integer of 0, 1 or 2;
with at least an equivalent amount of an acetal of cyanopropionaldehyde in the presence of at least an equivalent amount of sodium hydride to give the appropriately substituted 3-benzoyl-3-cyano-1-propionaldehyde acetal represented by the structural formula VI. The propionaldehyde intermediate is then reacted with at least an equivalent amount of hydroxylamine hydrochloride to give the appropriately substituted 2-aryl-1-hydroxypyrrole-3-carbonitrile represented by the structural formula VII. The reaction is conducted at an elevated temperature, preferably about 70° C. to 100° C.

Conversion of the 2-phenyl-1-hydroxypyrrole-3-carbonitrile or 2-(substituted phenyl)-1-hydroxypyrrole-3-carbonitrile to the corresponding 4-halo, 5-halo or 4,5-dihalo-2-(substituted phenyl)-1-hydroxypyrrole-3-carbonitrile, is readily achieved by reaction of the above said 2-phenyl-1-hydroxypyrrole-3-carbonitrile or 2-(substituted phenyl)-1-hydroxypyrrole-3-carbonitrile with at least one equivalent of bromine or a sulfuryl halide, in the presence of a solvent such as dioxane, tetrahydrofuran, acetic acid or a chlorinated hydrocarbon solvent. When sulfuryl chloride or sulfuryl bromide is used the reaction is generally conducted at temperatures below 40° C., preferably at about 0° C. to 30° C., but when elemental bromine is employed, the reaction is usually conducted at about 20° C.–50° C. Other halogenating agents that may be employed include sodium hypochlorite, t-butylhypochlorite, N-bromosuccinimide, N-iodosuccinimide and the like. The reactions are illustrated as follows:

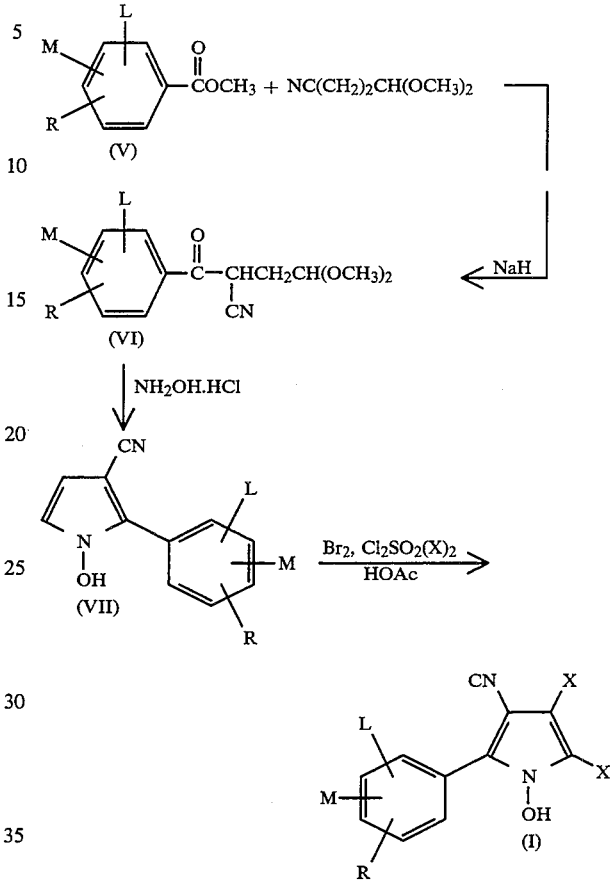

Certain of the 5-arylpyrrole-2,3-dicarbonitrile compounds of formula I may be prepared by reacting the oxime of 2-bromoacetophenone, or a substituted derivative thereof, with sodium oxalacetate to give phenacyloxalacetate 3-oxime or (substituted phenacyl)oxalacetate 3-oxime. The said oxalacetate intermediate is then reacted with hydrochloric acid in an alcohol to give a 5-aryl-1-hydroxypyrrole-3-carboxylate represented by structural formula VIII wherein $R_6$ is $C_1$–$C_6$ alkyl or $C_2$–$C_6$ cycloalkyl. The resultant hydroxypyrrole intermediate is reacted with methyl iodide and potassium t-butoxide to give 5-aryl-1-methoxypyrrole-3-carboxylate. Saponification of the thus- obtained carboxylate gives 5-aryl-1-methoxypyrrole-3-carboxylic acid. The thus obtained methoxypyrrole-3-carboxylic acid is then reacted with chlorosulfonyl isocyanate and dimethylformamide to give the formula I 5-aryl-1-methoxypyrrole-2,3-dicarbonitrile, which can be halogenated using standard procedures to give other compounds of formula I. This reaction scheme is illustrated as follows:

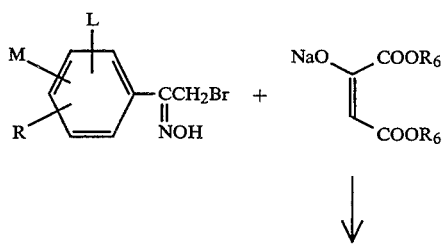

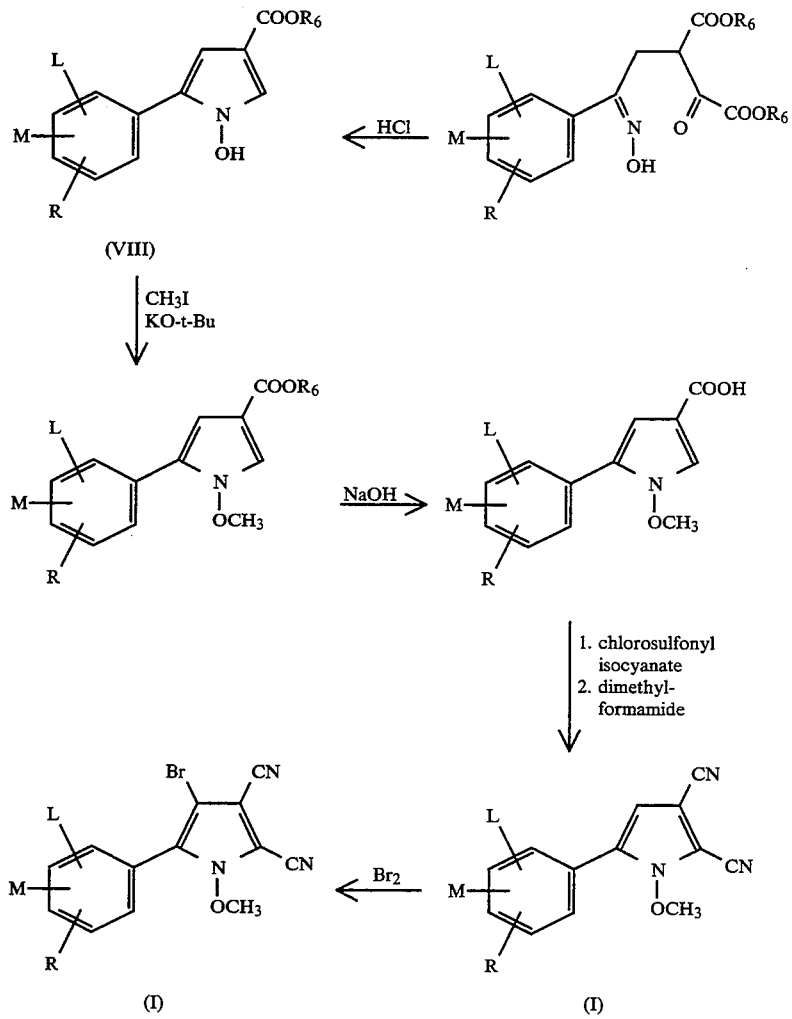

Similarly, the formula III 5-arylpyrrole-3-carbonitrile compounds of the present invention may be prepared by the sequential reaction of the above-mentioned ethyl 5-aryl-1-methoxypyrrole-3-carboxylate with bromine and then saponification to yield 2,4-dibromo-5-aryl-1-methoxypyrrole-3-carboxylic acid, which is then reacted with chlorosulfonyl isocyanate and dimethylformamide to give the formula III 2,4-dibromo-5-aryl-1-methoxypyrrole-3-carbonitrile. The reactions may be illustrated as follows:

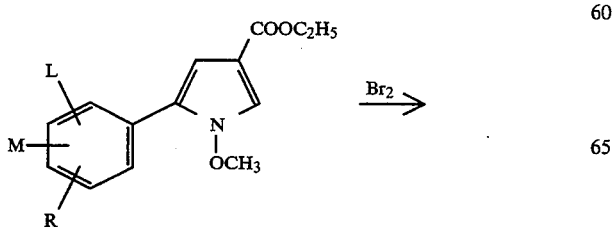

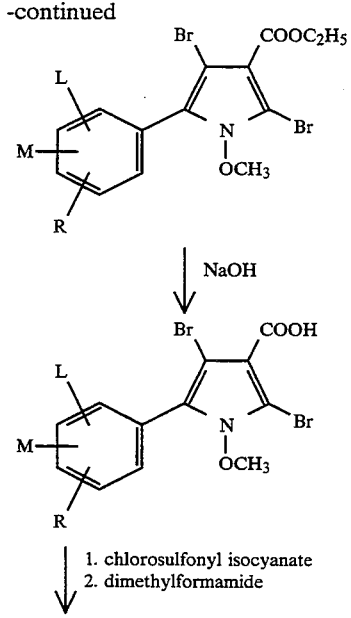

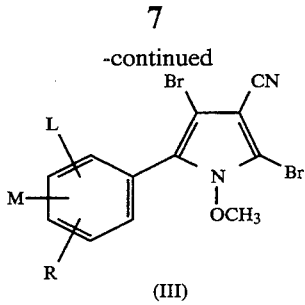

(III)

methyl iodide and potassium tert-butoxide to yield 5-aryl-1-methoxy-2-(trifluoromethyl)pyrrole-3-carboxylate. Bromination and saponification of said compound gives a 4-bromo-5-aryl-1-methoxy-2-(trifluoromethyl)-pyrrole-3-carboxylic acid intermediate which is then reacted with chlorosulfonyl isocyanate and dimethylformamide to give the 4-bromo-5-aryl-1-methoxy-2-(trifluoromethyl)pyrrole-3-carbonitrile compounds of formula III as illustrated below:

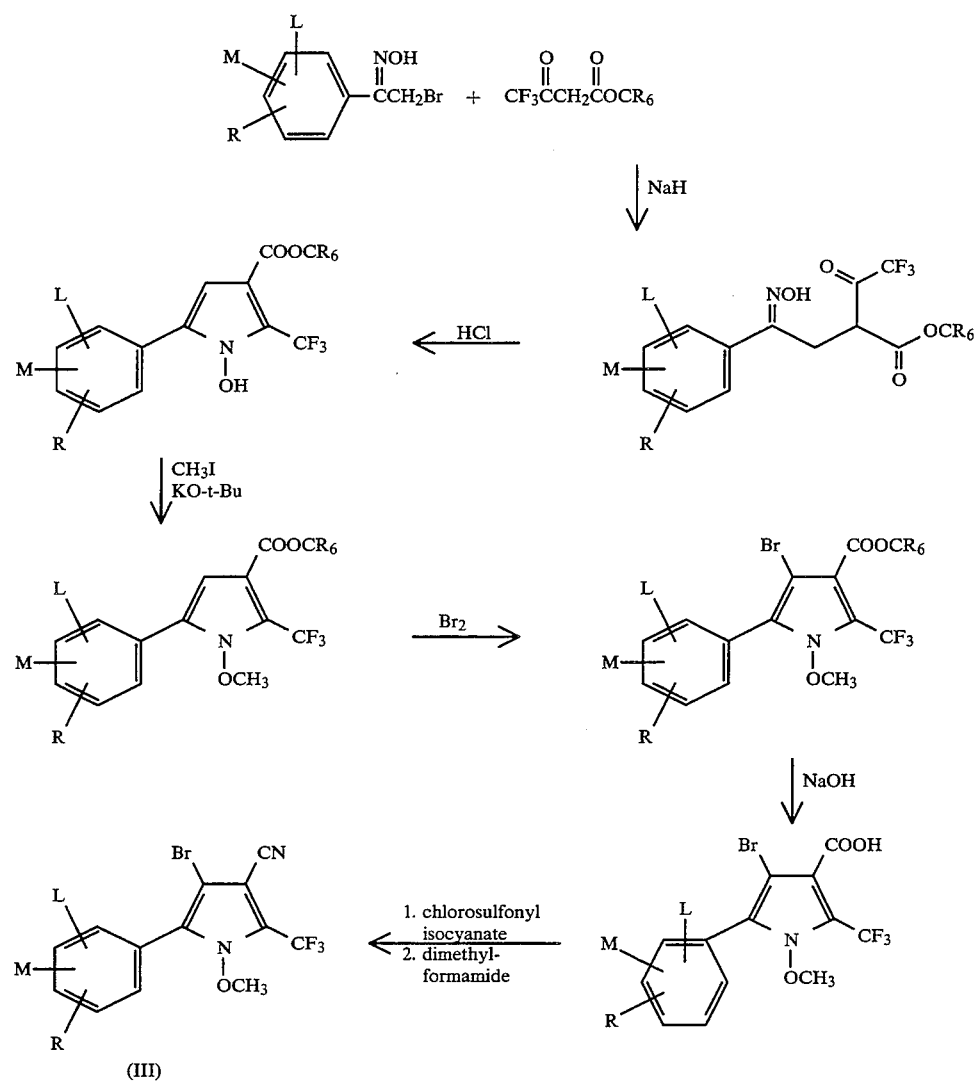

(III)

The formula III carbonitrile compounds of the present invention may also be prepared from the reaction of a trifluoroacetoacetate with the oxime of a substituted or unsubstituted a-bromoacetophenone in the presence of sodium hydride to give a 2-(substituted phenacyl)-4,4,4-trifluoroacetoacetate 2-oxime intermediate. The said acetoacetate intermediate is reacted with hydrochloric acid in an alcohol to form 5-aryl-1-hydroxy-2-(trifluoromethyl)pyrrole-3-carboxylate. The (trifluoromethyl)pyrrole-3-carboxylate is reacted with Preparation of formula IV 5-aryl-1-methoxypyrrole-2-carbonitrile compounds can be achieved by reaction of the above mentioned 5-aryl-1-methoxypyrrole-3-carboxylic acid, ethyl ester with chlorosulfonyl isocyanate and dimethylformamide to give 2-cyano-5-aryl-1-methoxypyrrole-3-carboxylic acid, ethyl ester. Saponification and bromination of the said methoxypyrrole-3-carboxylic acid, ethyl ester intermediate gives the formula IV, 3,4-dibromo-5-phenyl-1-methoxypyrrole-2-carbonitrile or 3,4-dibromo-5-(substituted phenyl)-1-methoxypyrrole-2-carbonitrile. This reaction scheme is illustrated as follows:

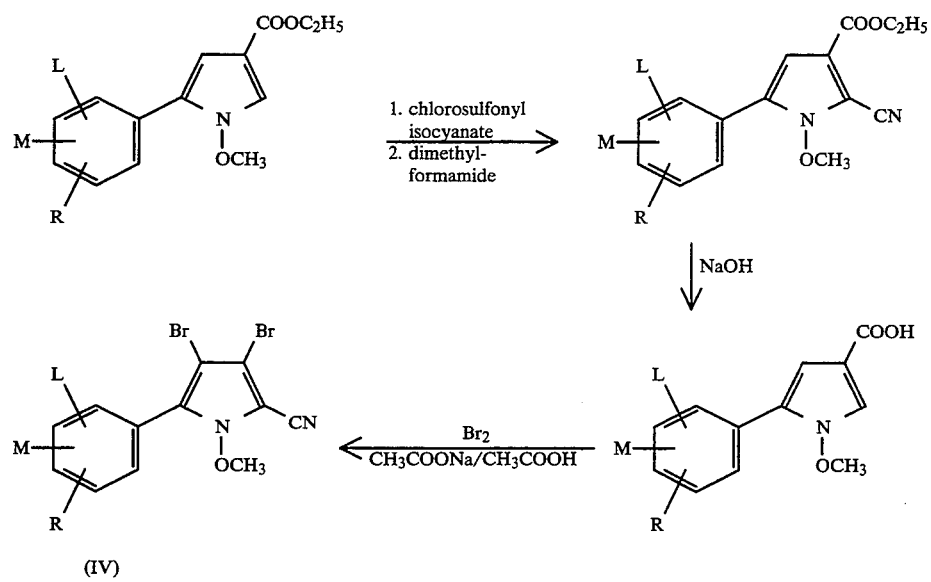
Similarly, other formula I N-oxygenated arylpyrroles may be prepared by the following reactions.
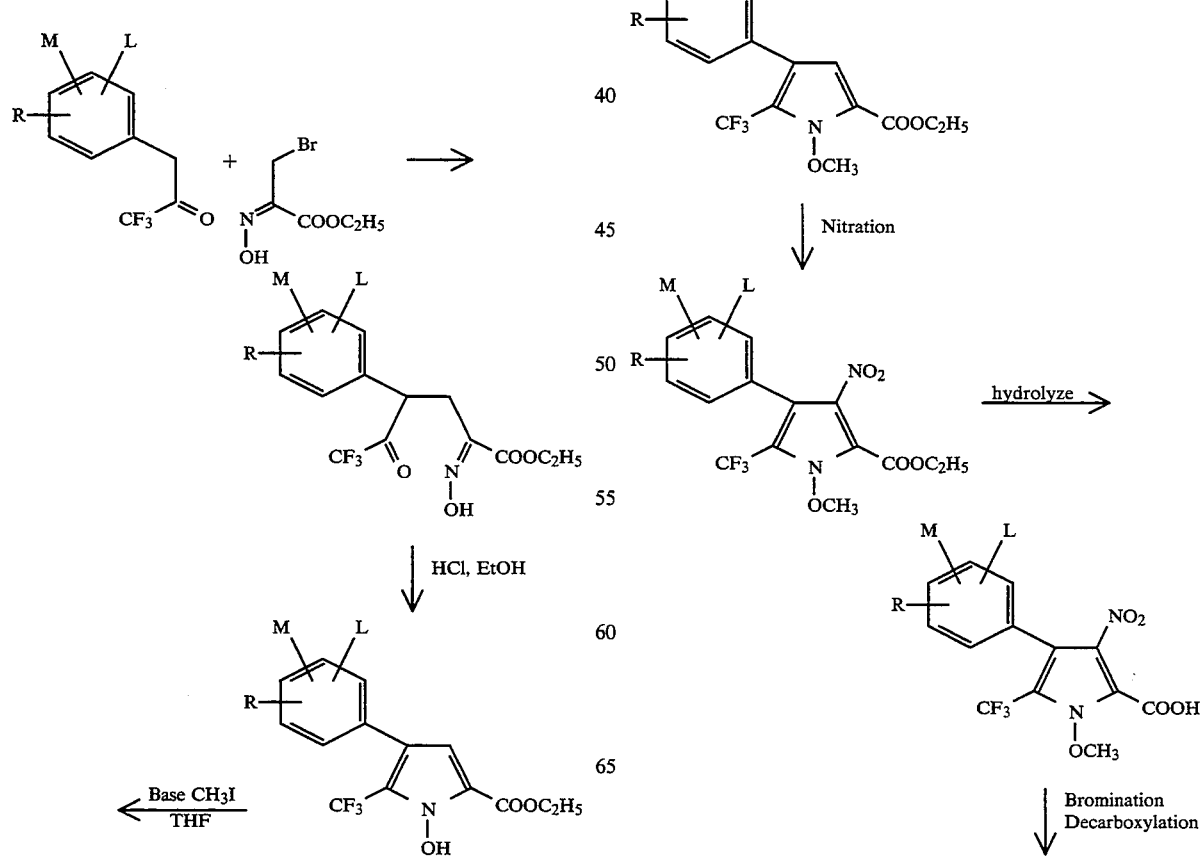

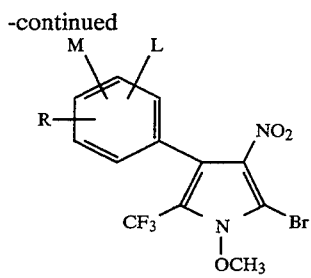

5

10

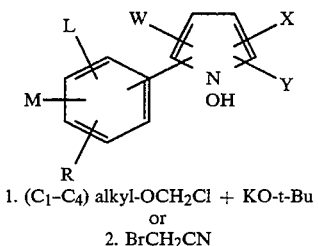

1. (C$_1$-C$_4$) alkyl-OCH$_2$Cl + KO-t-Bu
or
2. BrCH$_2$CN

Another method of preparing 3-aryl N-oxygenated pyrroles is the following:

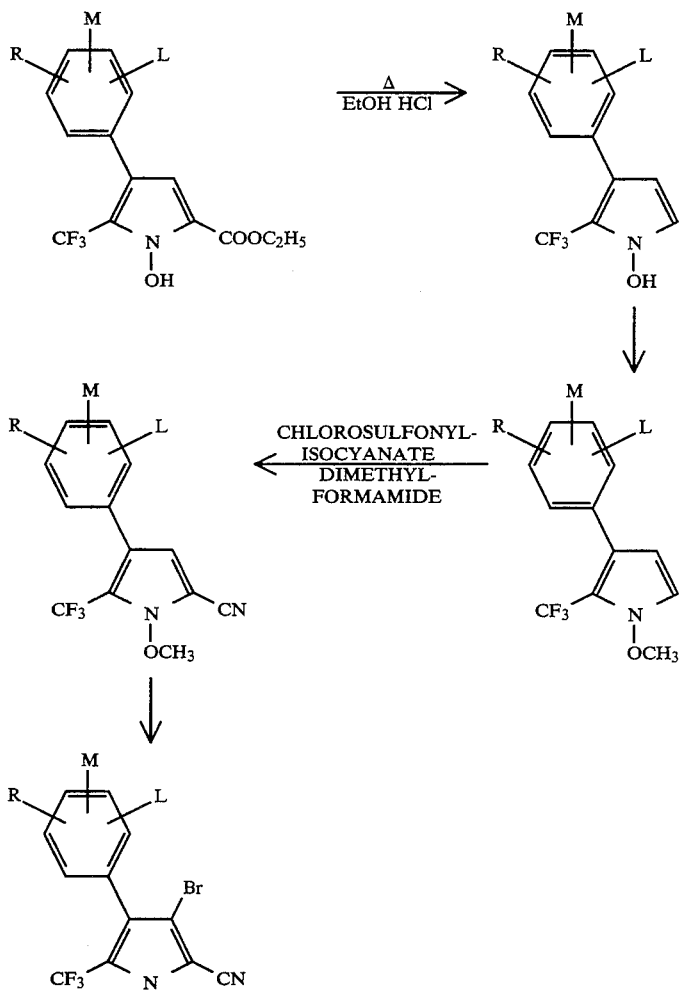

N-oxygenated arylpyrroles can be prepared by reaction of the appropriately substituted formula I N-oxygenated arylpyrrole, wherein A is hydrogen, and L, M, R, W, X and Y are as described above, with an appropriate alkylating agent and a suitable base, for example, a chloromethyl C$_1$-C$_4$ alkyl ether and potassium t-butoxide. This reaction provides an N-oxygenated arylpyrrole having the same substituents as the starting material, but in addition is substituted on the oxygen with C$_1$-C$_4$ alkoxymethyl. In a similar reaction bromoacetronitrile is substituted for the chloromethyl C$_1$-C$_4$ alkyl ether and yields the formula I N-oxygenated arylpyrrole with an acetonitrile substituent on the oxygen. The reactions may be illustrated as follows:

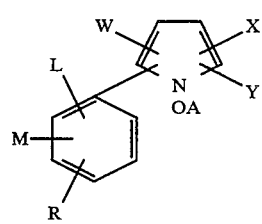

wherein L, M, R, W, X and Y are as described for formula I above and A is (1) C$_1$-C$_4$ alkoxymethyl or (2) CH$_2$CN.

Similarly, N-oxygenated arylpyrroles can be prepared by reaction of the appropriately substituted formula I N-oxygenated arylpyrrole, wherein A is hydrogen, and L, M, R, W, X and Y are as described above, with an appropriate acylating agent and a suitable base, for example, a $C_1$-$C_6$ acid chloride and potassium t-butoxide. This reaction provides an N-oxygenated arylpyrrole having the same substituents as the starting material, but in addition is substituted on the oxygen with $C_1$-$C_6$ alkanoyl. The reaction may be illustrated as follows:

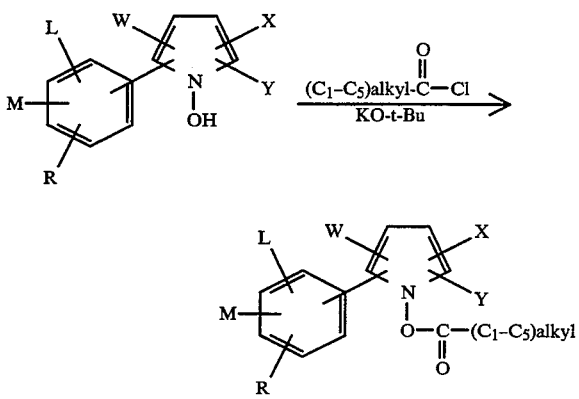

An intermediate useful in the preparation of N-oxygenated arylpyrroles has the structural formula IX:

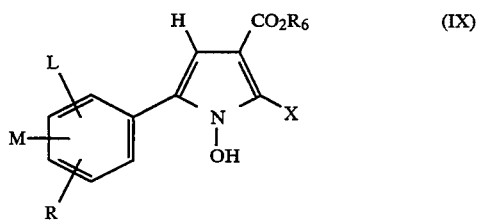

wherein
X is H or $CF_3$;
L is H, F, Cl or Br;
M and R are each independently H, $C_1$-$C_3$ alkyl, $C_1$-$C_3$ alkoxy, $C_1$-$C_3$ alkylthio, $C_1$-$C_3$ alkylsulfinyl, $C_1$-$C_3$ alkylsulfonyl, cyano, F, Cl, Br, I, nitro, $CF_3$, $R_1CF_2$, $R_2CO$ or $NR_3R_4$;
and when M and R are on adjacent positions and taken with the carbon atoms to which they are attached they may form a ring in which MR represents the structure:

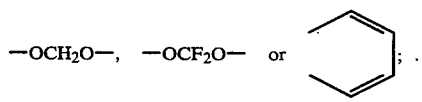

Z is $S(O)_n$ or O;
$R_1$ is H, F, $CHF_2$, CHFCl or $CF_3$;
$R_2$ is $C_1$-$C_3$ alkyl, $C_1$-$C_3$ alkoxy or $NR_3R_4$;
$R_3$ is H or $C_1$-$C_3$ alkyl;
$R_4$ is H, $C_1$-$C_3$ alkyl or $R_5CO$;
$R_5$ is H or $C_1$-$C_3$ alkyl; and
n is an integer of 0, 1 or 2; and
$R_6$ is hydrogen, $C_1$-$C_6$ alkyl or $C_3$-$C_6$ cycloalkyl.
The preparation of formula IX compounds is shown in previous illustrations, excepting when $R_6$ is hydrogen.

Hydrolysis of a formula IX compound when $R_6$ is not hydrogen yields another formula IX compound having the same structure except that $R_6$ is now hydrogen.

The N-oxygenated arylpyrroles of the present invention are effective for controlling insects, acarina and nematodes. These compounds are also effective for protecting growing or harvested crops from attack by the above-said pests.

In practice generally about 10 ppm to 10,000 ppm and preferably 100 ppm to about 5,000 ppm of a formula I N-oxygenated arylpyrrole, dispersed in water, or another inexpensive liquid carrier, is effective when applied to the plants, the crops or the soil in which said crops are growing to protect said crops from attack by insects, acarina and/or nematodes. These compounds are also useful for protecting turf grass from attack by pests such as grubs, chinch bugs and the like.

The formula I N-oxygenated arylpyrroles of this invention are also effective for controlling insects, nematodes and acarina, when applied to the foliage of plants and/or to the soil or water in which said plants are growing in sufficient amount to provide a rate of from about 0.100 kg/ha to 4.0 kg/ha of active ingredient.

While the N-oxygenated arylpyrroles of this invention are effective for controlling insects, nematodes and acarina when employed alone, they may also be used in combination with other biological chemicals, including other insecticides, nematicides and acaricides. For example, the N-oxygenated arylpyrroles of this invention may be used effectively in conjunction or combination with phosphates, carbamates, pyrethroids, formamidines, chlorinated hydrocarbons, halobenzoylureas and the like.

Advantageously, the above-said N-oxygenated arylpyrroles may be formulated into dry compacted granules, flowable compositions, granular formulations, wettable powders, dusts, dust concentrates, microemulsions and the like, all of which lend themselves to soil, water and/or foliage application and provide the requisite plant protection. Such formulations include the compounds of the invention admixed with inert, pharmacologically-acceptable solid or liquid diluents.

For example, wettable powders, dusts and dust concentrate formulations of the invention can be prepared by grinding together about 3% to 20%, by weight, of the formula I N-oxygenated arylpyrrole compound, with about 3% to 20% by weight of a solid anionic surfactant. One suitable anionic surfactant is a dioctyl ester of sodium sulfosuccinic acid, specifically Aerosol OTB ® surfactant marketed by the American Cyanamid Company. About 60% to 94%, by weight, of an inert solid diluent, such as montmorillonite, attapulgite, chalk, talc, kaolin, diatomaceous earth, limestone, silicates or the like also is used in such formulations.

Compacted granules especially useful for soil or water application can be prepared by grinding together in about equal parts, usually about 3 to 20 parts of the N-oxygenated arylpyrrole and a solid surfactant, with about 60 to 94 parts of gypsum. Thereafter, the mixture is compacted into small granular particles, about 24/48 mesh or larger.

Other suitable solid surfactants useful in the present formulations include not only the anionic dioctyl ester of sodium sulfosuccinic acid but also nonionic block copolymers of ethylene oxide and propylene oxide. Such block copolymers are marketed by BASF Wyandotte Corporation as Pluronic 10R8 ®, 17R8 ®, 25R8 ®, F38 ®, F68 ®, F77 ® or F87 ®, and are especially effective for the preparation of compacted granules.

In addition to the powders and concentrate formulations described hereinabove, wettable powders and flowables may be used because they may be dispersed in water. Preferably, such flowables will be applied at the locus with the aqueous compositions being sprayed on the foliage of plants to be protected. These sprays also may be applied to the breeding ground, food supply or habitat of the insects and acarina sought to be controlled.

Where solid formulations of the compounds of this invention are to be used in combination treatments with other pesticidal agents, the formulations can be applied as an admixture of the components or may be applied sequentially.

Similarly, liquid formulations of the N-oxygenated arylpyrrole in combination with other pesticidal agents may be tank mixed or may be applied separately, sequentially, as liquid sprays. Liquid spray formulations of the compounds of the invention should contain about 0.001% to 0.1% by weight of the active N-oxygenated arylpyrrole.

In order to facilitate a further understanding of the invention, the following examples are presented primarily for the purpose of illustrating more specific details thereof. The invention is not to be deemed limited thereby except as defined in the claims.

EXAMPLE 1

Preparation of starting material, 3-(p-Chlorobenzoyl)-3-cyano-1-propionaldehyde, dimethyl acetal

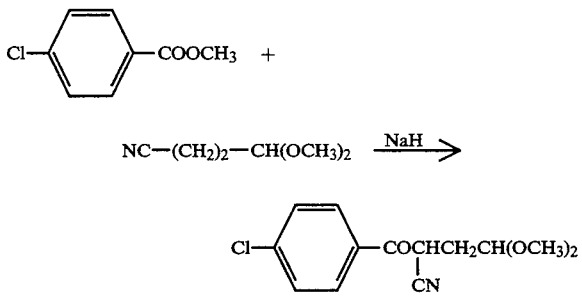

To a stirred slurry of sodium hydride (60% in mineral oil, 4.4 g, 0.11 mol) in anhydrous ethylene glycol dimethyl ether is added, dropwise, cyanopropionaldehyde dimethyl acetal (12.9 g, 0.1 mol). The resulting mixture is heated at 50° C. for 30 minutes, treated with a solution of p-chlorobenzoate methyl ester (17.1 g, 0.1 mol) in ethylene glycol dimethyl ether, heated at reflux temperature 12 hours, cooled to room temperature, quenched with isopropanol and concentrated in vacuo to give a liquid. The liquid is diluted with water, acidified with dilute hydrochloric acid and extracted with ether. The combined ether extracts are washed sequentially with water, saturated sodium bicarbonate solution, water and brine, dried over anhydrous sodium sulfate and concentrated in vacuo to give a liquid. The liquid is chromatographed using silica gel, methylene chloride and 3% ethyl acetate in methylene chloride as eluent to give the title compound as a yellow liquid (14.4 g, 54%), identified by IR and NMR spectral analysis.

Following the procedure described in Example 1, but using the appropriately substituted methyl phenylbenzoate, the compounds shown below are obtained.

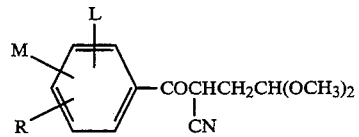

| L | M | R |
|---|---|---|
| H | 4-Cl | H |
| H | 3-Cl | 4-Cl |
| H | 4-CF$_3$ | H |

EXAMPLE 2

Preparation of 2-(p-Chlorophenyl)-1-hydroxypyrrole-3-carbonitrile

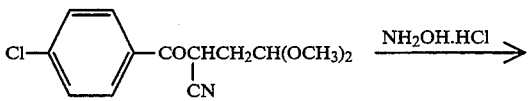

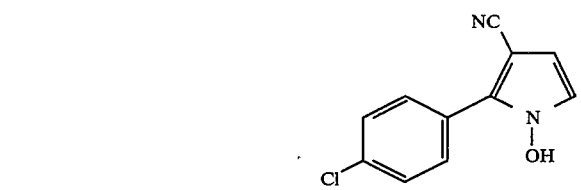

A stirred mixture of 3-(p-chlorobenzoyl)-3-cyano-1-propionaldehyde dimethyl acetal (10.0 g, 0.0373 mol) and hydroxylamine hydrochloride (3.89 g, 0.056 mol) in ethanol is heated to reflux temperature for one hour, cooled to room temperature and concentrated in vacuo to give a liquid. The liquid is dissolved in ether, washed sequentially with water and brine, dried over anhydrous sodium sulfate and concentrated in vacuo to yield a brown gum. The gum is chromatographed using silica gel, methylene chloride and 3% ethyl acetate in methylene chloride as eluent to give a brown solid. Recrystallization from methylene chloride/hexanes gives the title compound as a pale brown solid (6.0 g, 74%), mp 148.5°–150° C.

Following the procedure described in Example 2, but using the appropriately substituted 3-(benzoyl)-3-cyano-1-propionaldehyde dimethyl acetal, the compounds shown below are obtained.

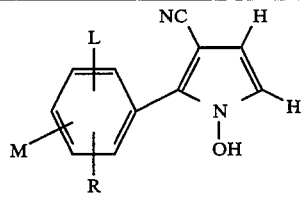

| L | M | R | mp °C. |
|---|---|---|---|
| H | 4-Cl | H | 148.5–150.0 |
| H | 3-Cl | 4-Cl | 207.0–208.0 |
| H | 4-CF$_3$ | H | 124.0–126.5 |

EXAMPLE 3

Preparation of
4,5-Dibromo-2-(p-chlorophenyl)-1-hydroxypyrrole-3-carbonitrile

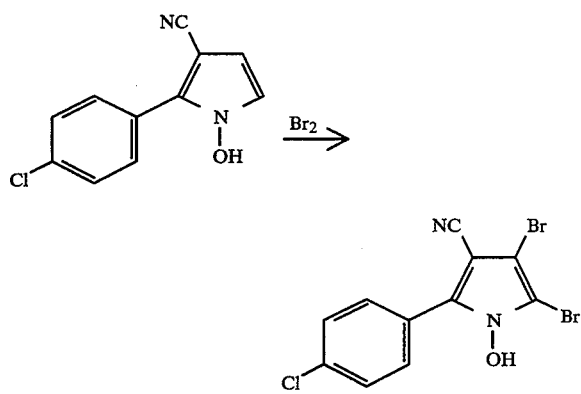

Bromine (2.3 g, 0.0144 mol) is added dropwise to a stirred solution of 2-(p-chlorophenyl)-1-hydroxypyrrole-3-carbonitrile (1.5 g, 0.007 mol) in dry p-dioxane at room temperature. After one hour, the reaction mixture is diluted with water and extracted with ether. The combined ether extracts are washed sequentially with water, saturated sodium bicarbonate solution, water and brine, dried over anhydrous sodium sulfate and concentrated in vacuo to give a solid. Recrystallization of the solid from ethyl acetate/hexanes gives the title compound as a white powder (1.98 g, 75%), mp 208°–209° C.

EXAMPLE 4

Preparation of
4,5-Dichloro-2-(p-chlorophenyl)-1-hydroxypyrrole-3-carbonitrile

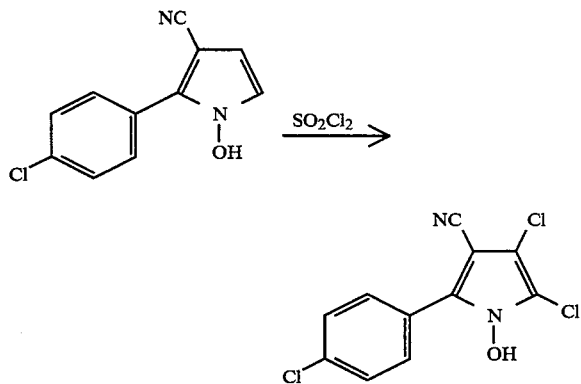

Sulfuryl chloride (1.95 g, 0.014 mol) is added dropwise to a stirred solution of 2-(p-chlorophenyl)-1-hydroxypyrrole-3-carbonitrile (1.5 g, 0.007 mol) in glacial acetic acid, the temperature rises to 45° C. and a yellow solid precipitates out. After 2½ hours the reaction mixture is diluted with water and extracted with ethyl acetate. The combined ethyl acetate extracts are washed sequentially with water, saturated sodium bicarbonate solution, water and brine, dried over anhydrous sodium sulfate and concentrated in vacuo to yield a brown solid. The solid is chromatographed using silica gel, methylene chloride and 3% ethyl acetate in methylene chloride as eluent to give the title compound as a brown powder (0.5 g, 25%), mp 156.5° C.

Following the procedure of either Example 3 or 4, but using the appropriately substituted 2-phenylpyrrole yields the following compounds.

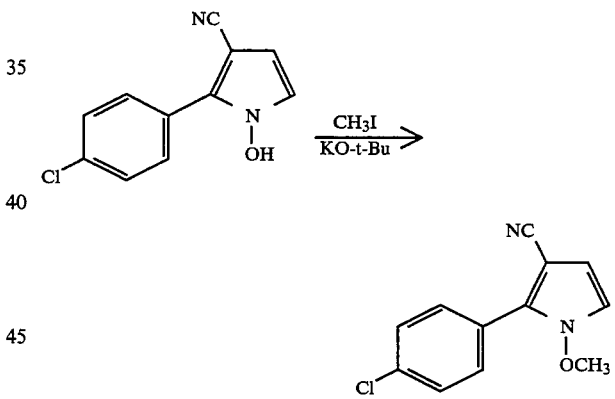

| A | L | M | R | Y | W | X | mp °C. |
|---|---|---|---|---|---|---|---|
| H | H | 4-Cl | H | Br | CN | Br | 208.0–209.0 |
| H | H | 3-Cl | 4-Cl | Br | CN | Br | 222.5–223.0 |
| H | H | 4-CF$_3$ | H | Br | CN | Br | 217.0–217.5 |
| CH$_3$ | H | 4-Cl | H | Br | Br | COOC$_2$H$_5$ | 98.0–101.0 |
| CH$_3$ | H | 4-Cl | H | CF$_3$ | Br | COOC$_2$H$_5$ | 47.0–50.0 |
| H | H | 4-Cl | H | Cl | CN | Cl | 156.5 |
| H | H | 3-Cl | 4-Cl | Cl | CN | Cl | 197.0–197.5 |

EXAMPLE 5

Preparation of
2-(p-Chlorophenyl)-1-methoxypyrrole-3-carbonitrile

To a stirred solution of 2-(p-chlorophenyl)-1-hydroxypyrrole-3-carbonitrile (2.88 g, 0.0132 mol) and anhydrous tetrahydrofuran is added potassium tert-butoxide (1.55 g, 0.0138 mol). After 30 minutes, methyl iodide (2.06 g, 0.9 mL, 0.0145 mol) is added and the resulting slurry is stirred at room temperature for 3 hours, diluted with water and extracted with ether. The combined ether extracts are washed sequentially with water and brine, dried over anhydrous magnesium sulfate and concentrated in vacuo to yield a solid. Crystallization of the solid from ether/hexanes gives the title compound as a brown solid (2.35 g, 77%), mp 105°–106° C.

Following the procedure described in Example 5, but using the appropriately substituted 2-phenyl-1-hydroxypyrrole-3-carbonitrile and the appropriate alkylating or acylating agent, the compounds shown below are obtained.

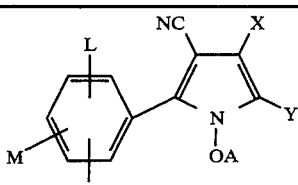

| A | L | M | R | X | Y | mp °C. |
|---|---|---|---|---|---|---|
| CH₂OC₂H₅ | H | 4-Cl | H | Cl | Cl | 75.0–76.5 |
| CH₂OC₂H₅ | H | 4-Cl | H | Br | Br | 75.0–76.0 |
| CH₂C≡CH | H | 4-Cl | H | Cl | Cl | 140.5–142.0 |
| $\underset{CN(CH_3)_2}{\overset{O}{\|}}$ | H | 4-Cl | H | Br | Br | 176.5–177.5 |
| CH₂CN | H | 4-Cl | H | Cl | Cl | 128.0–130.0 |
| $\underset{CCH_3}{\overset{O}{\|}}$ | H | 4-Cl | H | Br | Br | 129.5–131.0 |
| CH₃ | H | 3-Cl | 4-Cl | Cl | Cl | 152.0–156.0 |
| $\underset{CCH_2C(CH_3)_3}{\overset{O}{\|}}$ | H | 4-Cl | H | Br | Br | 131.5–132.0 |
| CH₂CN | H | 3-Cl | 4-Cl | Cl | Cl | 170.0–182.0 |
| $\underset{CC(CH_3)_3}{\overset{O}{\|}}$ | H | 4-Cl | H | Br | Br | 148.5–149.5 |
| CH₂CN | H | 4-Cl | H | Br | Br | 144.0–145.5 |
| CH₂C≡CH | H | 4-Cl | H | Br | Br | 145.0–147.0 |
| CHOCH₃<br>\|<br>CH₃ | H | 4-Cl | H | Br | Br | 110.0–112.0 |
| CH₃ | H | 3-Cl | 4-Cl | Br | Br | 183.0–184.0 |
| CH₂OC₂H₅ | H | 3-Cl | 4-Cl | Br | Br | 91.5–92.5 |
| CH₃ | H | 4-CF₃ | H | Br | Br | 204.5–207.5 |
| CH₃ | H | 4-Cl | H | Cl | Cl | 147.0–149.0 |

EXAMPLE 6

Preparation of 4,5-Dibromo-2-(p-chlorophenyl)-1-methoxypyrrole-3-carbonitrile

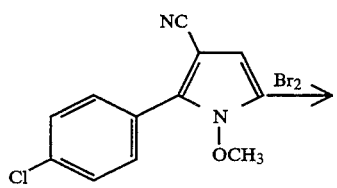

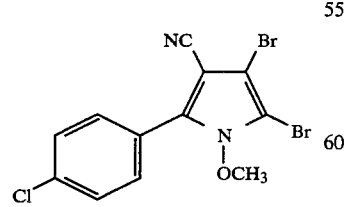

Bromine (2.16 g, 0.7 mL, 0.0135 mol) is added dropwise to a stirred solution of 2-(p-chlorophenyl)-1-methoxypyrrole-3-carbonitrile (1.5 g, 0.00645 mol) in anhydrous p-dioxane. After 3 hours, the reaction mixture is diluted with water and filtered. The solids are washed with water and dried to yield the title compound as a white solid (2.48 g, 98%), mp 190°–190.5° C.

EXAMPLE 7

Preparation of (p-Chlorophenacyl)oxalacetic acid, diethyl ester, 3-oxime

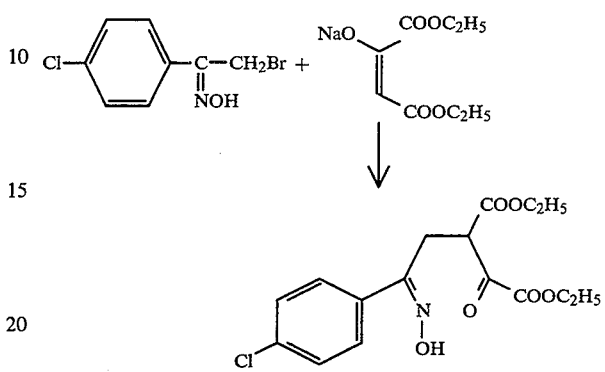

A solution of 2-bromo-4′-chloroacetophenone, oxime (24.9 g, 0.1 mol) in ethylene glycol dimethyl ether is added slowly to a 50° C. stirred solution of sodium diethyl oxalacetate (21.0 g, 0.1 mol) in ethylene glycol dimethyl ether. After the addition, the reaction mixture is heated at reflux temperature for 1 hour, cooled to room temperature and concentrated in vacuo to give a liquid. The liquid is dissolved in ether and washed sequentially with water and brine, dried over anhydrous sodium sulfate and concentrated in vacuo to yield a solid. Recrystallization from ether/hexanes gives the title compound as a white solid (18.0 g, 51%), mp 119°–120° C.

Following the procedure described in Example 7, but using the appropriately substituted 2-bromoacetophenone, oxime, the compounds shown below are obtained.

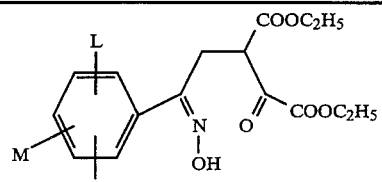

| L | M | R | mp °C. |
|---|---|---|---|
| H | 4-Cl | H | 119.0–120.0 |
| H | 3-Cl | 4-Cl | 99.5–104.0 |

EXAMPLE 6

Preparation of 5-(p-Chlorophenyl)-1-hydroxypyrrole-3-carboxylic acid, diethyl ester

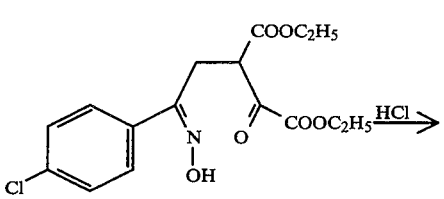

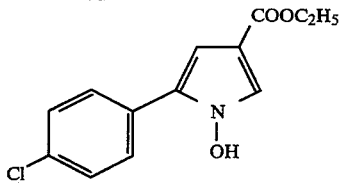

(p-Chlorophenyl)oxalacetic acid, diethyl ester, 3-oxime (26.0 g, 0.073 mol) in ethanol, saturated with HCl gas, is heated at reflux temperature for 90 minutes, cooled to room temperature, diluted with water and extracted with ether. The combined ether extracts are washed sequentially with water and brine, dried over anhydrous sodium sulfate and concentrated in vacuo to yield a gum. The gum is chromatographed using silica gel, methylene chloride and eluted sequentially with 1% ethyl acetate in methylene chloride and 3% ethyl acetate in methylene chloride to yield 2 products. The less polar fractions give 5-(p-chlorophenyl)-1-hydroxypyrrole-2,3-dicarboxylic acid, diethyl ester (7.3 g, 30%), mp 82°–84° C. Recrystallization from methylene chloride/hexanes, of the more polar fractions, gives the title compound as a white solid (10.5 g, 54%), mp 111°–116° C.

Following the procedures described in Example 8, but using the appropriately substituted phenacyloxalacetic acid, diethyl ester, 3-oxime, the compounds shown below are obtained.

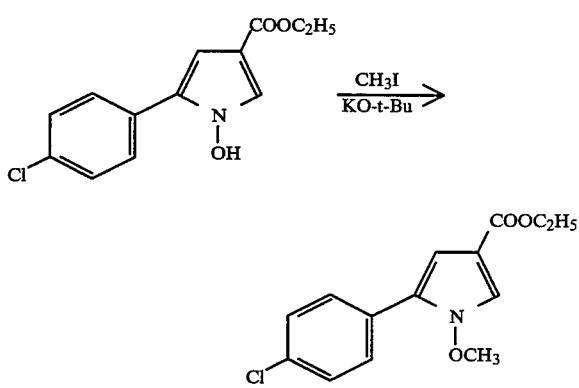

| L | M | R | mp °C. |
|---|---|---|---|
| H | 4-Cl | H | 111.0–116.0 |
| H | 3-Cl | 4-Cl | 146.0–148.0 |

EXAMPLE 9

Preparation of 5-(p-Chlorophenyl)-1-methoxypyrrole-3-carboxylic acid, ethyl ester

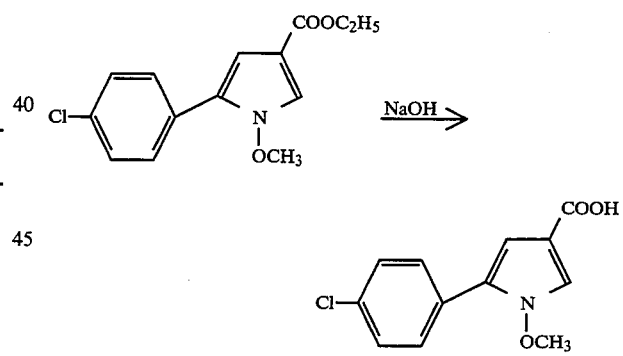

Potassium tert-butoxide (4.32 g, 0.0385 mol) is added portionwise to a 0° C. solution of ethyl 5-(p-chlorophenyl)-1-hydroxypyrrole-3-carboxylate (9.3 g, 0.035 mol) in anhydrous tetrahydrofuran. Methyl iodide (5.46 g, 0.0385 mol) is then added slowly to the solution at room temperature. The reaction mixture is stirred for 3 hours, diluted with water and extracted with ether. The combined ether extracts are washed sequentially with water and brine, dried over anhydrous sodium sulfate and concentrated in vacuo to give a solid. Crystallization from hexanes gives the title compound as a white crystalline solid (9.25 g, 94%), mp 65°–66° C.

Following the procedure described in Example 9, but using the appropriately substituted 2-phenyl-1-hydroxypyrrole, the compounds shown below are obtained.

| Y | L | M | R | mp °C. |
|---|---|---|---|---|
| H | H | 4-Cl | H | 65.0–66.0 |
| H | H | 3-Cl | 4-Cl | 69.5–72.5 |
| COOC$_2$H$_5$ | H | 4-Cl | H | 72.0–73.0 |
| CF$_3$ | H | 4-Cl | H· | 68.0–71.0 |

EXAMPLE 10

Preparation of 5-(p-Chlorophenyl)-1-methoxypyrrole-3-carboxylic acid

Sodium hydroxide (50%, 2.75 g, 0.0343 mol) in water is added to a stirred solution of ethyl 5-(p-chlorophenyl)-1-methoxypyrrole-2-carboxylate (8.0 g, 0.0286 mol) in ethanol. The reaction mixture is heated at reflux temperature for 2 hours, cooled to room temperature, diluted with water and extracted with ether. The aqueous layer is acidified with 10% hydrochloric acid and extracted with ether. The combined ether extracts are washed sequentially with water and brine, dried over anhydrous sodium sulfate and concentrated in vacuo to yield a solid which upon trituration with boiling hexanes gives the title compound as a white crystalline solid (7.0 g, 97%), mp 189°–191° C.

Following the procedure described in Example 10, but using the appropriately substituted 2-phenyl-1-methoxypyrrole, the compounds shown below are obtained.

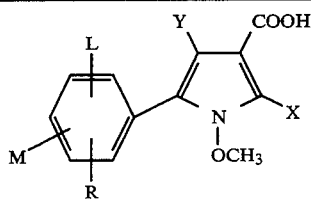

| L | M | R | Y | X | mp °C. |
|---|---|---|---|---|---|
| H | 4-Cl | H | H | H | 189.0–191.0 |
| H | 3-Cl | 4-Cl | H | CN | 221.5–226.5 |
| H | 4-Cl | H | Br | CF$_3$ | 215.0–217.0 |

EXAMPLE 11

Preparation of
5-(p-Chlorophenyl)-1-methoxypyrrole-2,3-dicarbonitrile

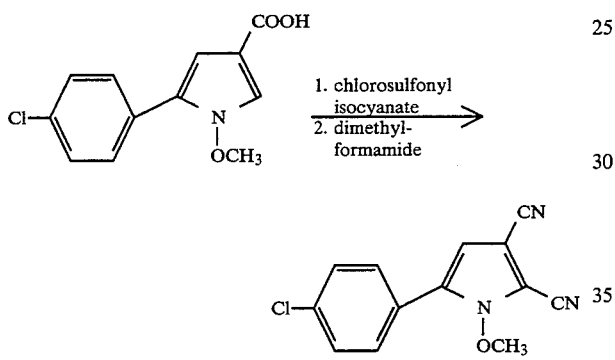

Chlorosulfonyl isocyanate (8.1 g, 0.0572 mol) is added dropwise to a 50° C. stirred mixture of 5-(p-chlorophenyl)-1-methoxypyrrole-3-carboxylic acid (6.0 g, 0.0238 mol) in acetronitrile and dimethylformamide. The reaction mixture is stirred at room temperature for 20 hours, cooled to 0° C., treated with dimethylformamide (9.2 mL), heated to 50° C. for 1 hour, cooled to room temperature for 3 hours, diluted with water and extracted with chloroform. The combined chloroform extracts are washed sequentially with water, saturated sodium bicarbonate solution, water and brine, dried over anhydrous sodium sulfate and concentrated in vacuo to give a gum. The gum is chromatographed using silica gel, and methylene chloride as eluent to give 2 products as a mixture. Crystallization from chloroform gives 2-(p-chlorophenyl)-1-methoxypyrrole-3,4-dicarbonitrile (1.1 g, 18%), as a yellow solid, mp 193°–194° C. The filtrate from the above crystallization is chromatographed using silica gel, and 30% ethyl acetate in heptane as eluent to give the title compound as a yellow solid (0.93 g, 15%), mp 126°–127° C.

Following the procedure described in Example 11, but using the appropriately substituted 2-phenyl-1-methoxypyrrole, the compounds shown below are obtained.

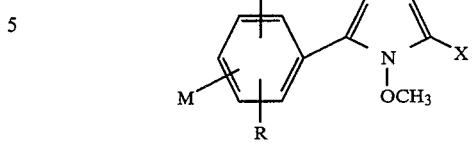

| L | M | R | X | Y | J | mp °C. |
|---|---|---|---|---|---|---|
| H | 4-Cl | H | CN | H | CN | 126.0–127.0 |
| H | 3-Cl | 4-Cl | CN | H | COOC$_2$H$_5$ | 128.0–130.5 |
| H | 4-Cl | H | CF$_3$ | Br | CN | 138.0–150.0 |

EXAMPLE 12

Preparation of
4-Bromo-5-(p-chlorophenyl)-1-methoxypyrrole-2,3-dicarbonitrile

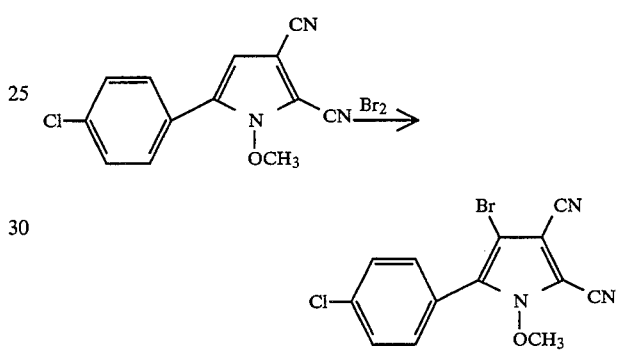

Bromine (0.341 g, 0.00213 mol) is added to a stirred mixture of 5-(p-chlorophenyl)-1-methoxypyrrole-2,3-dicarbonitrile (0.5 g, 0.00193 mol) and sodium acetate (0.318 g, 0.00388 mol) in acetic acid. The reaction mixture is heated at 95°–100° C. overnight, cooled to room temperature, diluted with water and extracted with ethyl acetate. The combined ethyl acetate extracts are washed sequentially with water, saturated sodium bicarbonate solution, aqueous sodium metabisulfite solution, water and brine, dried over anhydrous magnesium sulfate and concentrated in vacuo to yield a solid that is crystallized from ethyl acetate/hexanes to give the title compound as a yellow solid (0.406 g, 62%), mp 166.5°–167° C.

Following the procedure described in Example 12, but using the appropriately substituted 2-phenyl-1-methoxypyrrole, the compounds shown below are obtained.

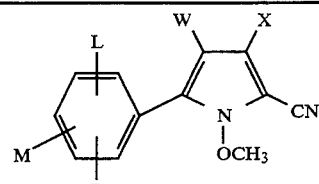

| L | M | R | W | X | mp °C. |
|---|---|---|---|---|---|
| H | 4-Cl | H | Br | CN | 166.5–167.0 |
| H | 4-Cl | H | CN | Br | 211.0–212.0 |

EXAMPLE 13

Preparation of
3,4-Dibromo-5-(3,4-dichlorophenyl)-1-methoxypyrrole-2-carbonitrile

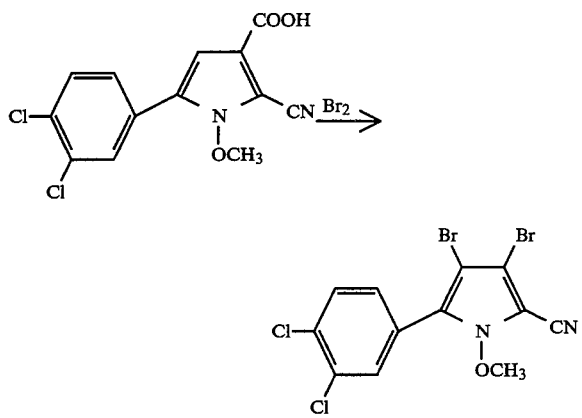

Bromine (1.13 g, 0.0071 mol) is added to a stirred solution of 2-cyano-5-(3,4-dichlorophenyl)-1-methoxypyrrole-3-carboxylic acid (1.0 g, 0.0032 mol) in glacial acetic acid. The reaction mixture is heated at reflux temperature for 2.5 hours, cooled to room temperature, diluted with water and extracted with ether. The combined ether extracts are washed sequentially with water, saturated sodium bicarbonate solution, water and brine, dried over anhydrous magnesium sulfate, and concentrated in vacuo to give a solid. Recrystallization of the solid from ether/hexanes yields the title compound as a white solid (0.46 g, 34%), mp 145°–150° C.

EXAMPLE 14

Preparation of
2,4-Dibromo-5-(p-chlorophenyl)-1-methoxypyrrole-3-carbonitrile

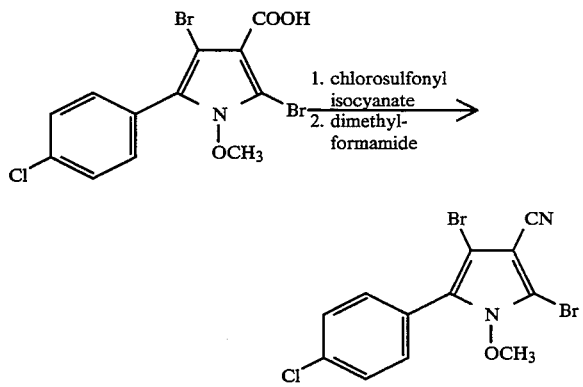

Chlorosulfonyl isocyanate (1.66 g, 0.0117 mol) is added to a 5° C. stirred solution of 2,4-dibromo-5-(p-chlorophenyl)-1-methoxypyrrole-3-carboxylic acid (2.0 g, 0.0049 mol) in acetronitrile. The solution is heated to 45°–50° C. for 2 hours, acetronitrile is added, cooled to 5° C. and dimethylformamide (1.9 mL, 0.0244 mol) is added. The reaction mixture is stirred at room temperature for 3 hours, diluted with water and extracted with chloroform. The combined chloroform extracts are washed sequentially with water and saturated sodium bicarbonate solution, dried over anhydrous magnesium sulfate and concentrated in vacuo to give a yellow solid. Chromatography using silica gel, methylene chloride and 3% ethyl acetate in methylene chloride as eluent yields the title compound as an off-white solid (0.23 g, 12%), mp 195°–197° C.

EXAMPLE 15

Preparation of
2-(p-Chlorophenacyl)-4,4,4-trifluoroacetic acid, ethyl ester, 2-oxime, (E)- and (Z)-

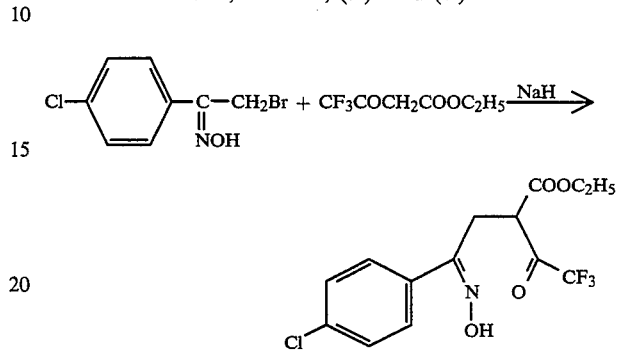

Under nitrogen, sodium hydride (60% in mineral oil, 3.04 g, 0.076 mol) is added portionwise to anhydrous ethylene glycol dimethyl ether and the mixture is heated to 40°–45° C. Ethyl trifluoroacetoacetate (14.0 g, 0.076 mol) is added dropwise over 30 minutes. Once the addition is complete, the reaction mixture is heated at 45°–50° C. for 1 hour and then a mixture of 2-bromo-4′-chloroacetophenone, oxime, (E)- (18 g, 0.0724 mol) in ethylene glycol dimethyl ether is added dropwise. The resulting slurry is heated at reflux temperature for 1 hour, cooled to room temperature and the solids are filtered off. The filtrate is concentrated in vacuo to give a solid residue which is dissolved in ether. The ether solution is washed sequentially with water and brine, dried over anhydrous magnesium sulfate and concentrated in vacuo to give a solid which is crystallized from ether/hexanes to yield the title compound as a white solid (17 g, 67%), mp 154°–154.5° C.

EXAMPLE 16

Preparation of
5-(p-Chlorophenyl)-1-hydroxy-2-(trifluoromethyl)pyrrole-3-carboxylic acid, ethyl ester

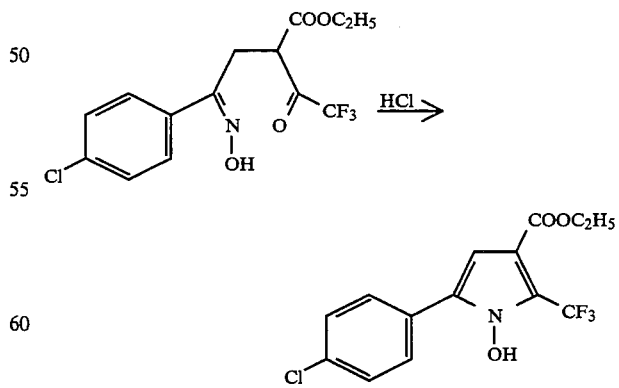

A stirred mixture of 2-(p-chlorophenacyl)-4,4,4-trifluoroacetic acid, ethyl ester, 2-oxime, (E)- and (Z)- (7.03 g, 0.02 mol) and ethanol, saturated with HCl gas, is heated at reflux temperature for 90 minutes. Excess HCl gas is removed by bubbling nitrogen through the reaction mixture at room temperature. The solvent is evaporated in vacuo and the residual solid is chromatographed using silica gel, methylene chloride and 3% ethyl acetate in methylene chloride as eluent to yield a solid. Crystallization from ethyl acetate/hexanes gives the title compound as a white solid (3.1 g, 46%), mp 161°–161.5° C.

EXAMPLE 17

Preparation of 5-(p-Chlorophenyl)-1-methoxy-4-nitro-2-(trifluoromethyl)pyrrole-3-carboxylic acid, ethyl ester

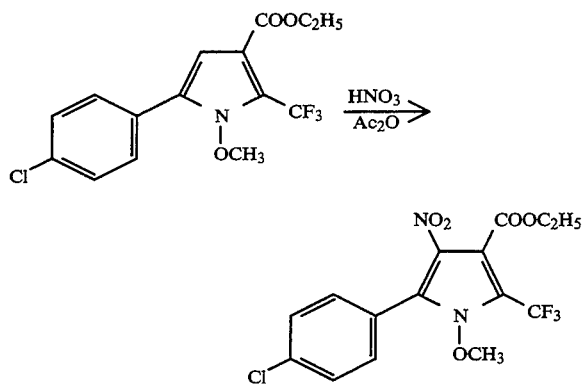

Fuming nitric acid (90%, 0.75 mL, 0.0167 mol) is added dropwise to a 5° C. solution of 5-(p-chlorophenyl)-1-methoxy-2-(trifluoromethyl)pyrrole-3-carboxylic acid, ethyl ester (3.27 g, 0.0094 mol) in acetic anhydride. After stirring at room temperature overnight, the reaction mixture is diluted with water and extracted with ether. The combined ether extracts are washed sequentially with water and brine, dried over anhydrous magnesium sulfate and concentrated in vacuo to give a thick yellow liquid. Chromatography using silica gel, methylene chloride and 2% ethyl acetate in methylene chloride as eluent gives a solid. Recrystallization from hexanes gives the title compound as a white solid (2.02 g, 55%), mp 90°–92° C.

Following the procedure described in Example 17, but using the appropriately substituted 2-phenyl-1-methoxypyrrole, the compounds shown below are obtained.

| Y | W | X | mp °C. |
|---|---|---|---|
| COOC$_2$H$_5$ | NO$_2$ | CF$_3$ | 90–92 |
| H | CN | NO$_2$ | 196–200 |
| NO$_2$ | CN | H | 175–184 |

EXAMPLE 18

Insecticide and acaricide evaluations

The following tests show the efficacy of the compounds as insecticides and acaricides. All tests are performed using technical materials and kept at 27° C. The test concentrations are in terms of active ingredient.

*Spodoptera eridania*, 3rd instar larvae, southern armyworm

A sieva lima bean leaf expanded to 7 to 8 cm in length is dipped in the test suspension with agitation for 3 seconds and placed in a hood to dry. The leaf is then placed in a 100×10 mm petri dish containing a damp filter paper on the bottom and 10 3rd instar caterpillars. The dish is maintained for 5 days before observations are made of mortality, reduced feeding, or any interference with normal moulting.

*Spodoptera eridania*, 7-day residual

The plants treated in the above test are maintained under high intensity lamps in the greenhouse for 7 days. These lamps duplicate the effects of a bright sunny day and are kept on for 14 hour day length. After 7 days, the foliage is sampled and assayed as in the above-said test.

*Aphis fabae*, mixed instar, bean aphid

Pots containing single nasturtium plants (Tropaeolum sp.) about 5 cm tall are infested with about 100 to 200 aphids one day before the test. Each pot is sprayed with the test formulation for 2 revolutions of a 4 rpm turntable in a hood, using a #154 DeVilbiss atomizer. The spray tip is held about 15 cm from the plant and the spray directed so as to give complete coverage of the plants and the aphids. The sprayed pots are set on their sides on white enamel trays and held for 2 days, following which mortality estimates are made.

*Tetranychus urticae* (P-resistant strain), 2-spotted spider mite

Sieva lima bean plants with primary leaves expanded to 7 to 8 cm are selected and cut back to one plant per pot. A small piece is cut from a leaf taken from the main colony and placed on each leaf of the test plants. This is done about 2 hours before treatment to allow the mites to move over to the test plant and to lay eggs. The size of the cut piece is varired to obtain about 100 mites per leaf. At the time of the treatment, the piece of leaf used to transfer the mites is removed and discarded. The mite-infested plants are dipped in the test formulation for 3 seconds with agitation and set in the hood to dry. Plant are kept for 2 days before estimates of adult kill are made using the first leaf. The second leaf is kept on the plant for another 5 days before observations are made of the kill of eggs and/or newly emerged nymphs.

*Diabrotic undecimpunctata howardi*, 3rd instar southern corn rootworm.

One cc of fine talc is placed in a 30 mL wide-mouth screw-top glass jar. One mL of the appropriate acetone suspension is pipetted onto the talc so as to provide 1.25 and 0.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed on a Vortex Mixer. Following this, 10 3rd instar rootworms are added to each jar and the jars are loosely capped to allow air exchange for the larvae. The treatments are held for 6 days before mortality counts are made. Missing larvae are presumed dead, since they decompose rapidly and can not be found. The concentrations used in this test correspond approximately to 50 and 10 kg/ha, respectively.

| Rating Scale: | |
|---|---|
| 0 = no effect | 5 = 56 to 65% kill |
| 1 = 10 to 25% kill | 6 = 66 to 75% kill |
| 2 = 26 to 35% kill | 7 = 76 to 85% kill |

Rating Scale:

| | |
|---|---|
| 3 = 36 to 45% kill | 8 = 86 to 99% kill |
| 4 = 46 to 55% kill | 9 = 100% kill |

Rating Scale:

R = reduced feeding

The data obtained for the above-described evaluations are reported in Table I.

TABLE I

| | Insecticide And Acaricide Evaluations | | | | | |
|---|---|---|---|---|---|---|
| | BEAN APHIDS | Southern Armyworm | | | P. RES MITES | SCRW[1] |
| Compound | (ppm) 100 | (ppm) 1000 | (ppm) 100 | 7 days | (ppm) 300 | (kg/ha) 50 |
| 4,5-Dibromo-2-(p-chlorophenyl)-1-hydroxypyrrole-3-carbonitrile | 0 | 9 | 9 | 9 | 0 | 0 |
| 4,5-Dichloro-2-(p-chlorophenyl)-1-hydroxypyrrole-3-carbonitrile | 0 | 9 | 9 | 9 | 0 | 0 |
| 4,5-Dibromo-2-(p-chlorophenyl)-1-methoxypyrrole-3-carbonitrile | 0 | 9 | 9 | 9 | 5 | 0 |
| 4,5-Dibromo-2-(p-chlorophenyl)-1-(ethoxymethoxy)-pyrrole-3-carbonitrile | 0 | 9 | 9 | 9 | 0 | 0 |
| 4,5-Dibromo-2-(p-chlorophenyl)-1-hydroxypyrrole-3-carbonitrile, dimethyl carbamate (ester) | 0 | 9 | 8 | 0 | 0 | 0 |
| 4,5-Dibromo-2-(p-chlorophenyl)-1-hydroxypyrrole-3-carbonitrile, acetate (ester) | 0 | 9 | 9 | 9 | 0 | 0 |
| 2-(p-Chlorophenyl)-1 methoxy-5-nitropyrrole-3-carbonitrile | 5 | 9 | 0 | 7 | 0 | 0 |
| 2-(p-Chlorophenyl)-1-methoxy-4-nitropyrrole-3-carbonitrile | 0 | 9 | 3 | 9 | 0 | 0 |
| 2-(p-Chlorophenyl)-1-methoxypyrrole-3,4-dicarbonitrile | 0 | 9 | 0 | 0 | 0 | 0 |
| 2-Bromo-5-(p-chlorophenyl)-1-methoxy-pyrrole-3,4-dicarbonitrile | 0 | 9 | 5 | 9 | 0 | 0 |
| 4,5-Dichloro-2-(p-chlorophenyl)-1-methoxypyrrole-3-carbonitrile | 0 | 9 | 9 | 9 | 0 | 0 |
| 4-Bromo-5-(p-chlorophenyl)-1-methoxy-2-(trifluoromethyl)-pyrrole-3-carbonitrile | 0 | 9 | 0 | 0 | 0 | 0 |
| 5-(p-Chlorophenyl)-1-methoxypyrrole-2,3-dicarbonitrile | 0 | 9 | 9 | 9 | 0 | 0 |
| 4-Bromo-5-(p-chlorophenyl)-1-methoxy-pyrrole-2,3-dicarbonitrile | 0 | 9 | 9 | 9 | 0 | 0 |
| 3,3-Dimethylbutyric acid, 2,3-dibromo-5-(p-chlorophenyl)-4-cyanopyrrol-1-yl ester | 0 | 9 | 9 | 9 | 0 | 0 |
| Pivalic acid, 2,3-dibromo-5-(p-chlorophenyl)-4-cyanopyrrol-1-yl ester | 9 | 9 | 9 | 9 | 0 | 0 |
| 4,5-Dibromo-2-(p-chlorophenyl)-1-(cyanomethoxy)-pyrrole-3-carbonitrile | 0 | 9 | 9 | 9 | 9 | 0 |
| 4,5-Dibromo-2-(p-chlorophenyl)-1-(2-propynyloxy)-pyrrole-3-carbonitrile | 0 | 9 | 9 | 9 | 0 | 0 |
| 4,5-Dibromo-2-(p-chlorophenyl)-1-(1-methoxy ethoxy)pyrrole-3-carbonitrile | 0 | 9 | 9 | 9 | 0 | 0 |
| 4,5-Dibromo-2-(3,4-dichlorophenyl)-1-hydroxypyrrole-3- | 0 | 9 | 0 | 9 | 0 | 0 |

TABLE I-continued

Insecticide And Acaricide Evaluations

| Compound | BEAN APHIDS (ppm) 100 | Southern Armyworm (ppm) 1000 | Southern Armyworm (ppm) 100 | Southern Armyworm 7 days | P. RES MITES (ppm) 300 | SCRW[1] (kg/ha) 50 |
|---|---|---|---|---|---|---|
| carbonitrile | | | | | | |
| 4,5-Dibromo-2-(3,4-dichlorophenyl)-1-methoxypyrrole-3-carbonitrile | 0 | 9 | 9 | 9 | 0 | 0 |
| 4,5-Dibromo-2-(3,4-dichlorophenyl)-1-(ethoxymethoxy)-pyrrole-3-carbonitrile | 0 | 9 | 9 | 9 | 0 | 0 |
| 4,5-Dichloro-2-(p-chlorophenyl)-1-(ethoxymethoxy)-pyrrole-3-carbonitrile | 0 | 9 | 9 | 9 | 0 | 0 |
| 4,5-Dichloro-2-(p-chlorophenyl)-1-(2-propynyloxy)-pyrrole-3-carbonitrile | 0 | 9 | 9 | 9 | 0 | 5 |
| 4,5-Dichloro-2-(p-chlorophenyl)-1-(cyanomethoxy)-pyrrole-3-carbonitrile | 0 | 9 | 9 | 9 | 0 | 0 |
| 4,5-Dichloro-2-(3,4-dichlorophenyl)-1-methoxypyrrole-3-carbonitrile | 0 | 9 | 9 | 9 | 0 | 0 |
| 4,5-Dichloro-2-(3,4-dichlorophenyl)-1-hydroxypyrrole-3-carbonitrile | 0 | 9 | 9 | 9 | 9 | 0 |
| 4,5-Dichloro-1-(cyanomethoxy)-2-(3,4-dichlorophenyl)-pyrrole-3-carbonitrile | 9 | 9 | 9 | 9 | 0 | 9 |
| 2,4-Dibromo-5-(p-chlorophenyl)-1-methoxy-pyrrole-3-carbonitrile | 7 | 9 | 9 | 0 | 9 | 5 |
| 1-(Benzyloxy)-4,5-dichloro-2-(p-chlorophenyl)pyrrole-3-carbonitrile | — | — | 9 | 0 | — | — |
| 3,4-Dibromo-5-(3,4-dichlorophenyl)-1-methoxypyrrole-2-carbonitrile | 0 | 9 | 9 | 9 | 0 | 0 |
| 4,5-Dibromo-1-hydroxy-2-(alpha,alpha,alpha-trifluoro-p-tolyl)-pyrrole-3-carbonitrile | 0 | 9 | 9 | 0 | 0 | 4 |
| 4,5-Dibromo-1-methoxy-2-(alpha,alpha,alpha-trifluoro-p-tolyl)-pyrrole-3-carbonitrile | 0 | 9 | 9 | 9 | 0 | 0 |

[1]SCRW = Southern Corn Rootworm

The above test results show the efficacy of the compounds as insecticides and acaricides.

EXAMPLE 19

The following tests show the efficacy of the compounds as insecticides. All tests are performed using technical materials and kept at 27° C. The test concentrations are in terms of active ingredient.

*Heliothis virescens*, 3rd instar tobacco budworm

Cotton cotyledons are dipped in the test formulation and allowed to dry in a hood. When dry, each is cut into quarters and ten sections placed individually in 30 mL plastic medicine cups containing a 5 to 7 mm long piece of damp dental wick. One 3rd instar caterpillar is added to each cup and a cardboard lid placed on the cup. Treatments are maintained for 3 days before mortality counts and estimates of reduction in feeding damage are made.

*Empoasca abrupta*, adults, western potato leafhopper

A Sieva lima bean leaf about 5 cm long is dipped in the test formulation for 3 seconds with agitation and placed in a hood to dry. The leaf is placed in a 100×10 mm petri dish containing a moist filter paper on the bottom. About 10 adult leafhoppers are added to each dish and the treatments are kept for 3 days before mortality counts are made.

*Blattella germanica*, bait test, adult male German cockroach

A 0.1% bait is prepared by pipetting 1 mL of a 1000 ppm solution of the test compound in acetone onto 1 gram of cornmeal in a 30 mL wide-mouth bottle. The bait is dried by passing a gentle stream of air into the bottle. The bait is placed in a 1 pint widemouth Mason jar and 10 adult male cockroaches are added. A screen lid is placed on the jar and a small piece of cotton soaked in 10% honey is put on the top of the screen lid. Mortality counts are made after 3 days.

*Blattella germanica,* residue test, adult male German cockroach

One mL of a 1000 ppm acetone solution of the test material is pipetted slowly over the bottom of a 150×15 mm petri dish so as to give as uniform coverage as possible. After the deposit has dried, 10 adult male cockroaches are placed in each dish and the lid is added. Mortality counts are made after 3 days.

*Spodoptera eridania,* systemic uptake, 3rd instar larvae, southern armyworm

The compound is formulated as an emulsion containing 0.1 gm of the test material, 0.2 gm of Emulphor EL-620, emulsifier, 10 mL of acetone and 90 mL of water. This is diluted 10-fold with water to give a 100 ppm emulsion for test. Subsequent 10-fold dilutions are made with water as needed. Sieva lima bean plants, with the primary leaves expanded to a length of 7 to 8 cm, are cut off at least 3 cm above the soil level to avoid contamination with soil bacteria that will cause decay of the stem during the test. The cut stems are placed in the test emulsions and each stem is wrapped with a bit of cotton to hold the stem off the bottom of the bottle and to limit evaporation and volatilization of the compound. The test is maintained for 3 days at 27° C. to allow the compounds to be taken up into the plant. Following this, one leaf is removed from the plant and placed in a 100×10 mm petri dish with 10 southern armyworms. Mortality counts and observations of feeding damage are made 3 and 5 days later.

*Empoasca abrupta,* adults, western potato leafhoppers, systemic uptake

The compound is formulated as an emulsion containing 0.1 gm of the test material, 0.2 gm of Emulphor EL-620, emulsifier, 10 mL of acetone and 90 mL of water. This is diluted 10 fold with water to give a 100 ppm emulsion for the test. Subsequent 10-fold dilutions are made with water as needed. Sieva lima bean plants, with the primary leaves expanded to a length of 7 to 8 cm, are cut off at least 3 cm above the soil level to avoid contamination with soil bacteria that will cause decay of the stem during the test. The cut stems are placed in the test emulsion and each stem is wrapped with a bit of cotton to hold the stem off the bottom of the bottle and to limit evaporation and volatilization of the compound. The test is maintained for 3 days at 27° C. to allow the compounds to be taken up into the plant. Following this, one leaf is removed from the plant and placed in a 100×10 mm petri dish with 10 adult western potato leafhoppers. After 3 days, mortality counts are made.

The rating scale for the above evaluations is the same as described in Example 18.

The data obtained are reported in Table II.

TABLE II

| | Insecticide Evaluations | | | | |
|---|---|---|---|---|---|
| | LEAF HOPPER | Tobacco Budworm | | G. COCKROACH | |
| | | | | Bait | Res |
| Compound | (ppm) 100 | (ppm) 1000 | (ppm) 100 | (ppm) 1000 | (ppm) 1000 |
| 4,5-Dibromo-2-(p-chloro-phenyl)-1-hydroxypyrrole-3-carbonitrile | 9 | 9 | 0 | 0 | 8 |
| 4,5-Dichloro-2-(p-chloro-phenyl)-1-hydroxypyrrole-3-carbonitrile | 9 | 9 | 0 | 0 | 0 |
| 4,5-Dibromo-2-(p-chloro-phenyl)-1-methoxypyrrole-3-carbonitrile | 0 | 9 | 0 | 0 | 0 |
| 4,5-Dibromo-2-(p-chloro-phenyl)-1-(ethoxymethoxy)-pyrrole-3-carbonitrile | 0 | 9 | 0 | 0 | 0 |
| 4,5-Dibromo-2-(p-chloro-phenyl)-1-hydroxypyrrole-3-carbonitrile, dimethyl carbamate (ester) | — | 0 | 0 | 0 | 0 |
| 4,5-Dibromo-2-(p-chloro-phenyl)-1-hydroxypyrrole-3-carbonitrile, acetate (ester) | — | 9 | 0 | 0 | 0 |
| 2-(p-Chlorophenyl)-1-methoxy-5-nitropyrrole-3-carbonitrile | 0 | 8 | 0 | 0 | 0 |
| 2-(p-Chlorophenyl)-1-methoxy-4-nitropyrrole-3-carbonitrile | 0 | 0 | 0 | 0 | 0 |
| 2-(p-Chlorophenyl)-1-methoxypyrrole-3,4-dicarbonitrile | — | 0 | — | 0 | 0 |
| 2-Bromo-5-(p-Chloro-phenyl)-1-methoxy-pyrrole-3,4-dicarbonitrile | 0 | 3 R3 | 3 R3 | 0 | 0 |
| 4,5-Dichloro-2-(p-chloro-phenyl)-1-methoxypyrrole-3-carbonitrile | — | 9 | 9 | 0 | 0 |
| 4-Bromo-5-(p-chloro-phenyl)-1-methoxy-2-(trifluoromethyl)-pyrrole-3-carbonitrile | 0 | — | 9 | 0 | — |
| 5-(p-Chlorophenyl)-1-methoxypyrrole-2,3-dicarbonitrile | 7 | 9 | 9 | 7 | 4 |
| 4-Bromo-5-(p-chloro- | 0 | 9 | 9 | 0 | 4 |

TABLE II-continued

| | Insecticide Evaluations | | | | |
| --- | --- | --- | --- | --- | --- |
| | LEAF HOPPER | Tobacco Budworm | | G. COCKROACH | |
| | | | | Bait | Res |
| Compound | (ppm) 100 | (ppm) 1000 | (ppm) 100 | (ppm) 1000 | (ppm) 1000 |
| phenyl)-1-methoxy-pyrrole-2,3-dicarbonitrile | | | | | |
| 3,3-Dimethylbutyric acid, 2,3-dibromo-5-(p-chlorophenyl)-4-cyanopyrrol-1-yl ester | 0 | 0 | 0 | 0 | 0 |
| Pivalic acid, 2,3-dibromo-5-(p-chlorophenyl)-4-cyanopyrrol-1-yl ester | 0 | 9 | 4 | 0 | 0 |
| 4,5-Dibromo-2-(p-chlorophenyl)-1-(cyanomethoxy)-pyrrole-3-carbonitrile | 0 | 9 | 9 | 0 | 0 |
| 4,5-Dibromo-2-(p-chlorophenyl)-1-(2-propynyloxy)-pyrrole-3-carbonitrile | 0 | 9 | 0 | 0 | 0 |
| 4,5-Dibromo-2-(p-chlorophenyl)-1-(1-methoxyethoxy)pyrrole-3-carbonitrile | 0 | 8 | 0 | 0 | 0 |
| 4,5-Dibromo-2-(3,4-dichlorophenyl)-1-hydroxypyrrole-3-carbonitrile | 0 | 9 | 4 | 0 | 7 |
| 4,5-Dibromo-2-(3,4-dichlorophenyl)-1-methoxypyrrole-3-carbonitrile | 0 | 9 | 0 | 0 | 2 |
| 4,5-Dibromo-2-(3,4-dichlorophenyl)-1-(ethoxymethoxy)-pyrrole-3-carbonitrile | 0 | 9 | 0 | 0 | 0 |
| 4,5-Dichloro-2-(p-chlorophenyl)-1-(ethoxymethoxy)-pyrrole-3-carbonitrile | 0 | 9 | 0 | 0 | 8 |
| 4,5-Dichloro-2-(p-chlorophenyl)-1-(2-propynyloxy)-pyrrole-3-carbonitrile | 0 | 9 | 7 | 0 | 0 |
| 4,5-Dichloro-2-(p-chlorophenyl)-1-(cyanomethoxy)-pyrrole-3-carbonitrile | 0 | 9 | 9 | 0 | 5 |
| 4,5-Dichloro-2-(3,4-dichlorophenyl)-1-methoxypyrrole-3-carbonitrile | 5 | 9 | 9 | 0 | 9 |
| 4,5-Dichloro-2-(3,4-dichlorophenyl)-1-hydroxypyrrole-3-carbonitrile | 0 | 9 | 9 | 0 | 9 |
| 4,5-Dichloro-1-(cyanomethoxy)-2-(3,4-dichlorophenyl)-pyrrole-3-carbonitrile | 3 | 9 | 9 | 0 | 0 |
| 2,4-Dibromo-5-(p-chlorophenyl)-1-methoxy-pyrrole-3-carbonitrile | 0 | — | 0 | — | — |
| 1-(Benzyloxy)-4,5-dichloro-2-(p-chlorophenyl)-pyrrole-3-carbonitrile | 0 | — | 0 | — | — |
| 3,4-Dibromo-5-(3,4-dichlorophenyl)-1-methoxypyrrole-2-carbonitrile | 4 | 9 | 8 | 0 | 0 |
| 4,5-Dibromo-1-hydroxy-2-(alpha,alpha,alpha-trifluoro-p-tolyl)-pyrrole-3-carbonitrile | 0 | 9 | 4 | 0 | 7 |
| 4,5-Dibromo-1-methoxy-2-(alpha,alpha,alpha-trifluoro-p-tolyl)-pyrrole-3-carbonitrile | 2 | 8 | 6 | 0 | 0 |

EXAMPLE 20

Evaluation of test compounds as nematicidal agents

Cultural Maintenance: Cultures of *C. Elegans* are maintained on *E. coli* lawns on NG Agar Plates at 20° C. New cultures are established weekly.

Nematodes for testing are washed from 4–5 day old cultures using Fresh Ascaris Ringers Solution (FARS). The worms are further washed with FARS, containing gentamycin, to reduce bacterial contamination and centrifuged to separate worms from wash solution. This procedure is repeated 3 times. The washed worms are then added to *C. briggsae* Maintenance Medium (CbMM), from GIBCOa to which is added gentamycin (600 units/mL) and mycostatin (0.5 mg/mL).

The tests are then made with mixtures of three compounds, piggy-backed from another high capacity screening program to reduce additional labor and compound expenditures.

Compounds are dissolved in acetone and made up to volume with water. The final test concentration of each compound in the mixture is 150 ppm. The test material is micropipetted (25 ul) into a single well of a 96-well sterile tissue culture plate (COSTAR)[b] and the solvent allowed to evaporate. These "treated" plates are used immediately or stored in a freezer without apparent adverse effects on the compounds.

A freshly prepared volume (50 ug) of *C. elegans* in CbMM is micropipetted into each treated well and several control wells per plate. Culture plates are incubated at 20° C.

Observations for efficacy are made under a dissecting microscope at 4, 24 and 48 hours post-immersion. Immediately prior to reading the plate, it is gently tapped to stimulate the movement of the worms. Activity is judged subjectively, but semi-quantitatively, based on the drug effects on motility of the adults and larvae. The criteria are as follows: 9=no motality, 8=no motality, 7=markedly reduced motility in approximately 95% of worms, 6=reduced motility, 5=slightly reduced motility, 0=normal motility, same as controls. Other factors indicating activity are easily noted such as death, rigor mortis, contraction, coiling, paralysis, abnormal twitching, reduced worm population in 48 hours and other deviation from normal behavior.

| PROCEDURE FOR *CAENORHABDITIS ELEGANS* ASSAY | |
|---|---|
| Day 0 | Inoculate *E. Coli*-NG Agar Dish With 30–50 *C. Elegans* Incubate At 20° C. |
| Day 4 | Harvest New *C. Elegans* Population Wash With Antibiotics Transfer to CbMM Add *C. Elegans* (25–100 UL) to "Medicated" Wells[a] Observe For Activity At 4 Hours Post-Immersion |
| Day 5 | Observe For Activity |
| Day 6 | Observe For Activity |

[a]Medicated Wells May Be Prepared Fresh Or Earlier And Stored In Freezer

Data obtained in these tests are reported in Table III below.

TABLE III

Nematicidal Evaluation

| | *C. Elegans* (150 ppm) | |
|---|---|---|
| | LARVA | ADULT |
| 4,5-Dichloro-2-(p-chlorophenyl)-1-hydroxypyrrole-3-carbonitrile | 7 | 7 |
| 4,5-Dichloro-2-(p-chlorophenyl)-1-(cyanomethoxy)pyrrole-3-carbonitrile | 8 | 8 |
| 4,5-Dichloro-1-(cyanomethoxy)-2-(3,4-dichlorophenyl)pyrrole-3-carbonitrile | 9 | 9 |
| 2,4-Dibromo-5-(p-chlorophenyl)-1-methoxypyrrole-3-carbonitrile | 0 | 0 |
| 2-(p-Chlorophenyl)-1-methoxy-4-nitropyrrole-3-carbonitrile | 0 | 0 |

What is claimed is:

1. A compound useful in the preparation of N-oxygenated arylpyrroles having the structural formula:

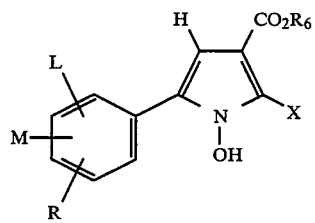

wherein

X is H or $CF_3$;

L is H, F, Cl or Br;

M and R are each independently H, $C_1$–$C_3$ alkyl, $C_1$–$C_3$ alkoxy, $C_1$–$C_3$ alkylthio, $C_1$–$C_3$ alkylsulfinyl, $C_1$–$C_3$ alkylsulfonyl, cyano, F, Cl, Br, I, nitro, $CF_3$, $R_1CF_2Z$, $R_2CO$ or $NR_3R_4$; and when M and R are on adjacent positions and taken with the carbon atoms to which they are attached they may form a ring in which MR represents the structure:

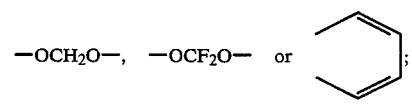

Z is $S(O)_n$ or O;

$R_1$ is H, F, $CHF_2$, CHFCl or $CF_3$;

$R_2$ is $C_1$–$C_3$ alkyl, $C_1$–$C_3$ alkoxy or $NR_3R_4$;

$R_3$ is H or $C_1$–$C_3$ alkyl;

$R_4$ is H, $C_1$–$C_3$ alkyl or $R_5CO$;

$R_5$ is H or $C_1$–$C_3$ alkyl; and n is an integer of 0, 1 or 2; and $R_6$ is hydrogen, $C_1$–$C_6$ alkyl or $C_3$–$C_6$ cycloalkyl.

* * * * *